(12) United States Patent
McCarthy et al.

(10) Patent No.: US 8,473,042 B2
(45) Date of Patent: Jun. 25, 2013

(54) TACHYARRHYTHMIA DETECTION USING DYNAMIC DURATION

(75) Inventors: Jason McCarthy, Weirton, WV (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 392 days.

(21) Appl. No.: 12/794,346

(22) Filed: Jun. 4, 2010

(65) Prior Publication Data

US 2010/0317984 A1    Dec. 16, 2010

Related U.S. Application Data

(60) Provisional application No. 61/187,216, filed on Jun. 15, 2009.

(51) Int. Cl.
*A61B 5/0464* (2006.01)

(52) U.S. Cl.
USPC ............... 600/518; 607/4; 607/14; 607/25

(58) Field of Classification Search
USPC ................................. 600/518; 607/4, 14, 25
See application file for complete search history.

(56) References Cited

U.S. PATENT DOCUMENTS

| | | | |
|---|---|---|---|
| 5,480,414 A | 1/1996 | Stroebel et al. |
| 5,814,085 A | 9/1998 | Hill |
| 5,817,133 A | 10/1998 | Houben |
| 5,891,170 A | 4/1999 | Nitzsche et al. |
| 5,941,831 A | 8/1999 | Turcott |
| 5,978,707 A | 11/1999 | Krig et al. |
| 6,151,524 A | 11/2000 | Krig et al. |
| 6,233,485 B1 | 5/2001 | Armstrong et al. |
| 6,317,632 B1 | 11/2001 | Krig et al. |
| 6,493,579 B1 | 12/2002 | Gilkerson et al. |
| 6,510,343 B2 | 1/2003 | Armstrong et al. |
| 6,567,691 B1 | 5/2003 | Stadler |

(Continued)

FOREIGN PATENT DOCUMENTS

WO    WO-2010147773 A1    12/2010

OTHER PUBLICATIONS

Wilkoff, Bruce, et al., "Strategic Programming of Detection and Therapy Parameters in Implantable Cardioverter-Defibrillators Reduces Shocks in Primary Prevention Patients", *J. Am. Coll. Cardiol. 52*(7), (Aug. 2008), p. 541-550.

(Continued)

*Primary Examiner* — Carl H Layno
*Assistant Examiner* — Michael Carey
(74) *Attorney, Agent, or Firm* — Schwegman Lundberg & Woessner, P.A.

(57) ABSTRACT

An apparatus comprises an implantable cardiac signal sensing circuit configured to produce a sensed cardiac signal representative of cardiac activity of a subject and a controller communicatively coupled to the cardiac signal sensing circuit. The controller includes a sensing module configured to detect a cardiac depolarization using the sensed cardiac signal and an arrhythmia detection module. The arrhythmia detection module is configured to detect a depolarization rate or interval that satisfies a first tachyarrhythmia detection rate zone threshold, adjust a specified detection duration threshold for the tachyarrhythmia detection zone according to the detected depolarization rate, declare that the detected depolarization rate is an episode of tachyarrhythmia when the detected depolarization rate is sustained for the adjusted detection duration threshold, and provide an indication of the tachyarrhythmia to a user or process.

22 Claims, 3 Drawing Sheets

U.S. PATENT DOCUMENTS

| | | |
|---|---|---|
| 6,658,286 B2 | 12/2003 | Seim |
| 6,678,560 B1 | 1/2004 | Gilkerson et al. |
| 6,889,081 B2 | 5/2005 | Hsu |
| 6,920,356 B2 | 7/2005 | Armstrong et al. |
| 7,103,405 B2 | 9/2006 | Sarkar et al. |
| 7,113,824 B2 * | 9/2006 | Krig et al. ............. 607/14 |
| 7,120,491 B1 | 10/2006 | Bailin et al. |
| 7,228,176 B2 | 6/2007 | Smith et al. |
| 7,346,388 B2 | 3/2008 | Elahi et al. |
| 7,580,741 B2 | 8/2009 | Cazares et al. |
| 2004/0059238 A1 * | 3/2004 | Fischell et al. ........... 600/515 |
| 2005/0149135 A1 | 7/2005 | Krig et al. |
| 2006/0281998 A1 | 12/2006 | Li |
| 2007/0135848 A1 | 6/2007 | Kim et al. |
| 2007/0142737 A1 | 6/2007 | Cazares et al. |
| 2007/0219456 A1 | 9/2007 | Thompson |
| 2008/0015651 A1 | 1/2008 | Ettori et al. |
| 2008/0051843 A1 * | 2/2008 | Li et al. ..................... 607/9 |
| 2008/0281370 A1 | 11/2008 | Lin et al. |
| 2008/0288009 A1 | 11/2008 | Kim et al. |
| 2009/0157126 A1 | 6/2009 | Perschbacher et al. |
| 2009/0163966 A1 | 6/2009 | Perschbacher et al. |
| 2009/0234400 A1 | 9/2009 | Krig et al. |

OTHER PUBLICATIONS

"International Application Serial No. PCT/US2010/037460, International Preliminary Report on Patentability mailed Dec. 29, 2011", 8 pgs.

"International Application Serial No. PCT/US2010/037460, International Search Report mailed Aug. 24, 2010", 4 pgs.

"International Application Serial No. PCT/US2010/037460, Written Opinion mailed Aug. 24, 2010", 6 pgs.

* cited by examiner

TACHYARRHYTHMIA DETECTION USING DYNAMIC DURATION

CROSS REFERENCE TO RELATED APPLICATION

This application claims the benefit of U.S. Provisional Patent Application Ser. No. 61/187,216, filed on Jun. 15, 2009, the specification of which is herein incorporated by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. Some IMDs detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

When detected, ventricular tachyarrhythmia can be terminated with high-energy shock therapy delivered with an ICD. Cardioversion/defibrillation therapy can cause patient discomfort and consumes a relatively large amount of battery power which may lead to a shortened useful device lifetime. Therefore, it is important to accurately detect tachyarrhythmia.

OVERVIEW

This document relates generally to systems, methods, and devices for monitoring cardiac function of a patient or subject, and in particular for improved detection of heart arrhythmias.

In example 1, an apparatus includes an implantable cardiac signal sensing circuit configured to produce a sensed cardiac signal representative of cardiac activity of a subject and a controller communicatively coupled to the cardiac signal sensing circuit. The controller includes a sensing module configured to detect a cardiac depolarization using the sensed cardiac signal and an arrhythmia detection module. The arrhythmia detection module is configured to detect a depolarization rate or interval that satisfies a first tachyarrhythmia detection rate zone threshold, adjust a specified detection duration threshold for the tachyarrhythmia detection zone according to the detected depolarization rate, declare that the detected depolarization rate is an episode of tachyarrhythmia when the detected depolarization rate is sustained for the adjusted detection duration threshold, and provide an indication of the tachyarrhythmia to a user or process.

In example 2, the apparatus of example 1 optionally includes a memory circuit included with or communicatively coupled to the controller. The memory circuit stores detection duration values indexed by depolarization rate or depolarization interval. The arrhythmia detection module is configured to determine the detection duration threshold using a detection duration value determined using the index.

In example 3, the arrhythmia detection module of any one or more of examples 1 or 2 is optionally configured to calculate the adjusted detection duration threshold as a function of the detected depolarization rate and a base detection duration value. The base detection duration value is specified according to the tachyarrhythmia detection rate zone threshold.

In example 4, the arrhythmia detection module of any one or more of examples 1-3 is optionally configured to determine that a detected depolarization rate or interval falls within one of a plurality of specified tachyarrhythmia detection rate zones, and adjust the detection duration threshold for the tachyarrhythmia rate zone according to the detected depolarization rate or interval. The arrhythmia detection module is configured to determine a plurality of detection durations within each of two or more of the tachyarrhythmia detection rate zones.

In example 5, the apparatus of any one or more of examples 1-4 optionally includes a different specified base detection duration value for each of at least two of the tachyarrhythmia detection rate zones. The arrhythmia detection module is configured to calculate an adjusted detection duration threshold as a function of the detected depolarization rate or interval and a base detection duration value for the particular tachyarrhythmia detection rate zone in which the detected depolarization rate or interval falls.

In example 6, the arrhythmia detection module of example 5 is optionally configured to calculate the adjusted duration threshold by reducing the specified base detection duration value for a tachyarrhythmia detection rate zone as a function of the detected depolarization rate or interval.

In example 7, the arrhythmia detection module of any one or more of examples 1-6 is optionally configured to calculate a central tendency of the depolarization rate or intervals, and adjust the detection duration threshold according to the calculated central tendency.

In example 8, the arrhythmia detection module of any one or more of examples 1-7 is optionally configured to adjust an initial detection duration threshold as a function of an initial detected depolarization rate or interval, re-detect a tachyarrhythmia when a re-detected depolarization rate or interval satisfies a specified tachyarrhythmia re-detection rate zone threshold, and adjust a re-detection duration threshold as a function of the re-detected depolarization rate. The re-detection duration threshold is capable of being different from the initial detection duration for a given depolarization rate or interval.

In example 9, the apparatus of any one or more of claims 1-8 optionally includes a therapy circuit communicatively coupled to the controller and configured to provide an anti-tachyarrhythmia therapy. The arrhythmia detection module determines whether the declared tachyarrhythmia episode is sustained during a specified sustained rate duration (SRD), and the controller is configured to initiate a delivery of an anti-tachyarrhythmia therapy in response to an expiration of the SRD during which the declared tachyarrhythmia episode is sustained.

In example 10, the arrhythmia detection module of example 9 is optionally configured to re-detect, after the anti-tachyarrhythmia therapy ceases, a depolarization rate or interval that satisfies a specified tachyarrhythmia re-detection rate zone threshold, and adjust a post-therapy detection duration threshold as a function of the re-detected depolarization rate or interval. The arrhythmia detection module is configured to be capable of calculating the post-therapy detection duration threshold as a different function of the depolarization rate or interval than an initial detection duration threshold.

In example 11, the arrhythmia detection module of any one or more of examples 1-10 is optionally configured to classify the tachyarrhythmia, and adjust the detection duration threshold according to the determined tachyarrhythmia classification.

In example 12, a method includes detecting, using an IMD, a cardiac depolarization rate or depolarization interval that satisfies a specified tachyarrhythmia detection rate zone threshold, adjusting a detection duration threshold according to the detected depolarization rate or interval, declaring that the detected depolarization rate is an episode of tachyarrhythmia when the detected depolarization rate is sustained for the adjusted detection duration threshold, and providing an indication of the tachyarrhythmia to a user or process. A plurality of detection durations is determinable by the IMD for rates or intervals within the tachyarrhythmia detection zone.

In example 13, the adjusting the detection duration threshold of example 12 optionally includes determining the adjusted detection duration threshold according to an index by the detected depolarization rate or interval.

In example 14, the method of any one or more examples 12 or 13 optionally includes specifying a base detection duration value. The adjusting the detection duration threshold optionally includes calculating the adjusted detection duration threshold as a function of the detected depolarization rate or interval and the base detection duration value.

In example 15, the method of any one or more of examples 12-14 optionally includes determining that the detected depolarization rate falls within one of a plurality of specified tachyarrhythmia detection rate zones, and declaring detection of an episode of tachyarrhythmia when the detected depolarization rate is sustained for a time interval that meets or exceeds the adjusted detection duration threshold for the tachyarrhythmia detection rate zone into which detected depolarization rate falls. The determining the detection duration optionally comprises using one of a plurality of detection durations that are determinable for depolarization rates or intervals within a single tachyarrhythmia detection rate zone.

In example 16, the method of example 15 optionally includes specifying a different base detection duration value for different tachyarrhythmia detection rate zones. The adjusting the detection duration threshold optionally includes calculating the adjusted detection duration threshold as a function of the detected depolarization rate or interval and the base detection duration value for the tachyarrhythmia rate zone into which detected depolarization rate falls.

In example 17, the adjusting the detection duration threshold of example 16 optionally includes reducing the specified base detection duration value as a function of the detected depolarization rate or interval.

In example 18, the adjusting a detection duration threshold according to the detected depolarization rate or interval of any one or more of examples 12-17 optionally includes calculating a central tendency of the depolarization rate or intervals, and adjusting the detection duration threshold according to the calculated central tendency.

In example 19, the adjusting a detection duration threshold of any one or more of examples 12-18 optionally includes adjusting an initial detection duration threshold as a function of an initial detected depolarization rate or interval, and the method of the examples optionally includes re-detecting a tachyarrhythmia when a re-detected depolarization rate or satisfies a specified tachyarrhythmia re-detection rate zone threshold, and adjusting a re-detection duration threshold as a function of the re-detected depolarization rate. The re-detection duration threshold is capable of being different from the initial detection duration threshold for a given depolarization rate or interval.

In example 20, the method of any or more of examples 12-19 optionally includes determining whether the declared tachyarrhythmia episode sustains during a specified sustained rate duration (SRD), and initiating a delivery of an anti-tachyarrhythmia therapy in response to an expiration of the SRD during which the declared tachyarrhythmia episode is sustained.

In example 21, the method of example 20 optionally includes re-detecting, after the anti-tachyarrhythmia therapy ceases, a depolarization rate or interval that satisfies a specified tachyarrhythmia re-detection rate zone threshold, and adjusting a post-therapy duration detection threshold as a function of the re-detected depolarization rate or interval. The post-therapy detection duration threshold is capable of being calculated as a different function of the depolarization rate or interval than the initial detection duration threshold.

In example 22, the method of any one or more of examples 12-22 optionally includes classifying the tachyarrhythmia. The adjusting a detection duration threshold optionally includes adjusting the detection duration threshold according to the determined tachyarrhythmia classification.

In example 23, an apparatus comprises an implantable cardiac signal sensing circuit configured to produce a sensed cardiac signal representative of cardiac activity of a subject, a controller communicatively coupled to the cardiac signal sensing circuit, a memory circuit included with or communicatively coupled to the controller, and a therapy circuit communicatively coupled to the controller. The controller includes a sensing module configured to detect a cardiac depolarization using the sensed cardiac signal, and an arrhythmia detection module. The arrhythmia detection module is configured to detect a depolarization rate or interval that satisfies a first tachyarrhythmia detection rate zone threshold, adjust a specified detection duration threshold for the tachyarrhythmia detection zone according to the detected depolarization rate, declare detection of an episode of tachyarrhythmia when the detected depolarization rate is sustained for a period of time that meets or exceeds the adjusted detection duration threshold, and provide an indication of the detected episode of tachyarrhythmia to a user or process. The detection duration threshold is adjustable to a plurality of values for depolarization rates or intervals within the same tachyarrhythmia detection rate zone. The memory circuit is configured to store detection duration values indexed by depolarization rate or depolarization interval, and the arrhythmia detection module is configured to determine the detection duration threshold using a detection duration value determined using the index. The therapy circuit is configured to provide an anti-tachyarrhythmia therapy. The arrhythmia detection module is configured to determine whether the declared tachyarrhythmia episode is sustained during a specified sustained rate duration (SRD), and the controller is configured to initiate a delivery of an anti-tachyarrhythmia therapy in response to an expiration of the SRD during which the declared tachyarrhythmia episode is sustained.

In example 24, the arrhythmia detection module of example 23 is optionally configured to re-detect, after the anti-tachyarrhythmia therapy ceases, a depolarization rate or interval that satisfies a specified tachyarrhythmia re-detection rate zone threshold, and adjust a post-therapy detection duration threshold as a function of the re-detected depolarization rate or interval. The arrhythmia detection module is configured to be capable of calculating the post-therapy detection duration threshold as a different function of the depolarization rate or interval than an initial detection duration threshold.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for improved detection of cardiac events by an IMD. Specifically systems and methods for improved detection of arrhythmias by an IMD are described.

An IMD may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
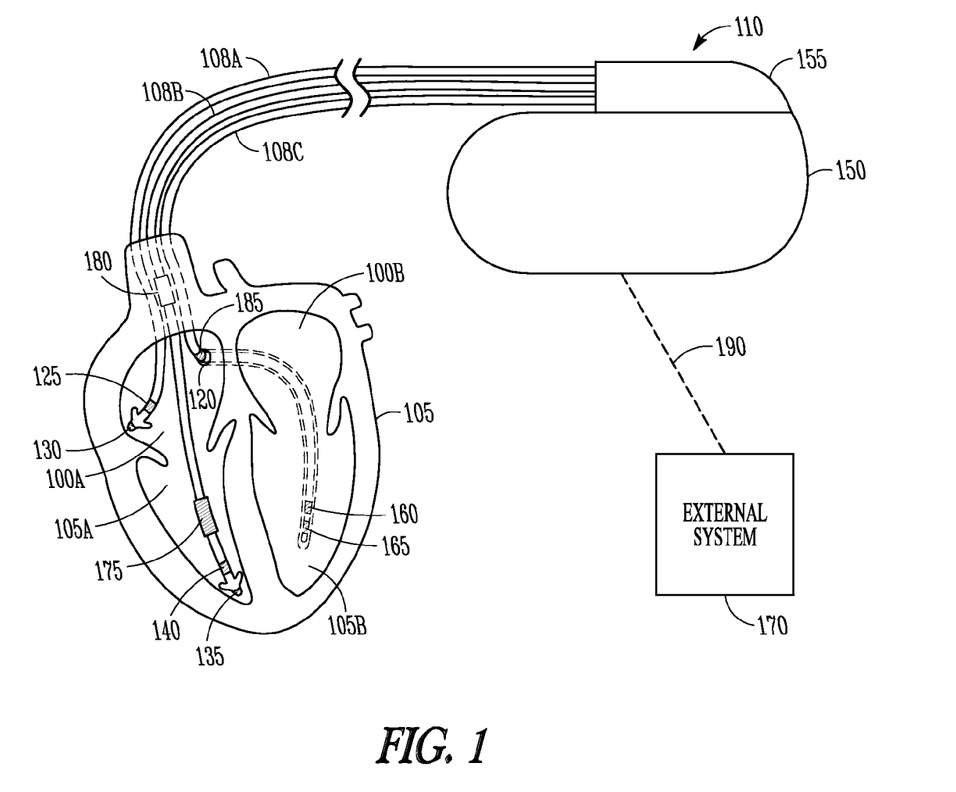
FIG. 1 is an illustration of an example of portions of a system that includes an IMD.

FIG. 1 is an illustration of portions of a system that uses an IMD 110. Examples of IMD 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Atrial lead 108A includes electrodes (electrical contacts, such as ring electrode 125 and tip electrode 130) disposed in an atrium 100A of heart 105 for sensing signals, or delivering pacing therapy, or both, to the atrium 100A.

Ventricular lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105.

The IMD 110 may include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein. The third cardiac lead 108C may include a ring electrode 185 positioned near the coronary sinus (CS) 120.

Lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110.

IMDs, such as ICDs for example, typically detect tachyarrhythmia when a heart rate suddenly exceeds a specified threshold heart rate. The term specified refers to a parameter being a hard-set fixed value as well as being a programmable parameter whose value is set with a device programmer. Typically, ICDs divide the spectrum of possible heart rates into detection rate zones. For the ICD to deem that the detected heart rate zone may indicate an episode tachyarrhythmia, the heart rate has to exceed the rate threshold for the detection zone and remain within the zone for a specified time duration.

For example, if an ICD detects that a heart rate falls within a detection zone that defines ventricular tachycardia and the time that the heart is in that zone satisfies the duration requirement, the ICD may then trigger other detection methods to confirm that a patient is indeed experiencing ventricular tachycardia.

Different detection zones may have different requirements for the duration. However, the duration requirement is typically the same for all of the heart rates within one heart rate zone. Table 1 shows an example of three tachyarrhythmia detection zones and associated durations.

TABLE 1

| Heart Rate Zone | Heart Rate Range (bpm) | Duration (sec) |
|---|---|---|
| Zone 1 | 170-199 | 60 |
| Zone 2 | 200-249 | 12.5 |
| Zone 3 | 250+ | 2.5 |

In the example, the lowest tachyarrhythmia detection rate zone threshold is 170 beats per minute (bpm) and corresponds to Zone 1. This tachyarrhythmia detection rate zone may correspond to a slow-VT detection zone. Zone 2 is 200-249 bpm and may correspond to a VT detection zone. Zone 3 is for rates above 250 bpm and may correspond to a VF detection zone.

Figure 2:
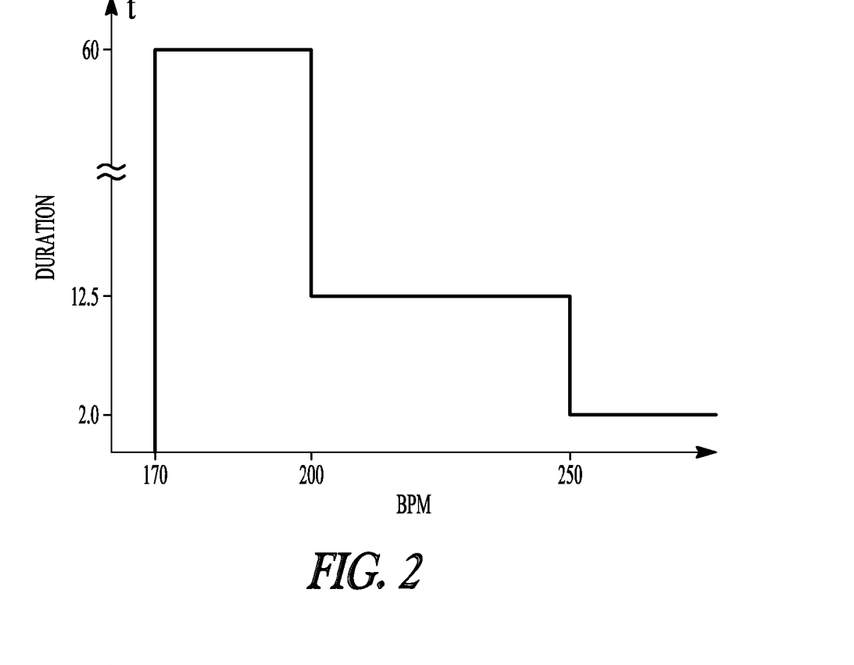
FIG. 2 is a graph showing heart rate zones using one duration for an entire zone.

Using one duration for an entire zone can cause a drastic change in duration requirements at the boundaries. For example, in the Table a heart rate of 199 bpm falls within Zone 1, which has an associated duration of 60 seconds before a possible episode of tachyarrhythmia is declared by the IMD. A heart rate of 200 bpm satisfies the threshold for Zone 2, which has an associated duration of only 12.5 seconds. Thus, a heart rate of 199 bpm has to be sustained for 60 seconds before the device declares a possible episode of tachyarrhythmia, while a heart rate of 200 bpm only has to be sustained for 12.5 seconds before a possible episode is declared, even though the difference in rate is very subtle (only 1 bpm). This is shown graphically in FIG. 2.

A better approach may be to allow multiple different durations within the heart rate zones. This will provide duration requirements with less drastic changes in duration times due to subtle changes in heart rate occurring near the heart rate zone boundaries.

Figure 3:
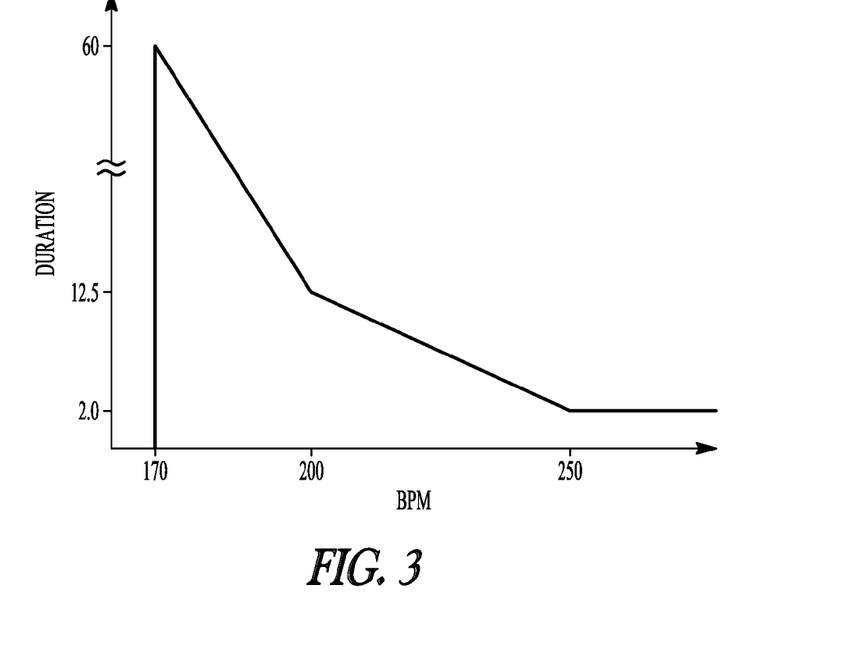
FIG. 3 shows an example of multiple different durations within the heart rate zones.

FIG. 3 shows an example of multiple different durations within the heart rate zones. In this example, each heart rate in the lowest two zones of the Table (from 170 to 200 bpm) has a unique duration. For example, heart rates of 205 bpm and 210 bpm will still be in the VT detection rate zone, but the time duration a heart rate of 205 bpm needs to stay in the zone is slightly longer than the time duration a heart of 210 bpm needs to stay in the zone before a possible episode of VT is declared. Thus, the duration is more dynamic and changes more frequently according to the heart rate. This allows a change in duration to be as subtle as the change in heart rate, and prevents the drastic change in duration at the zone boundaries.

Figure 4:
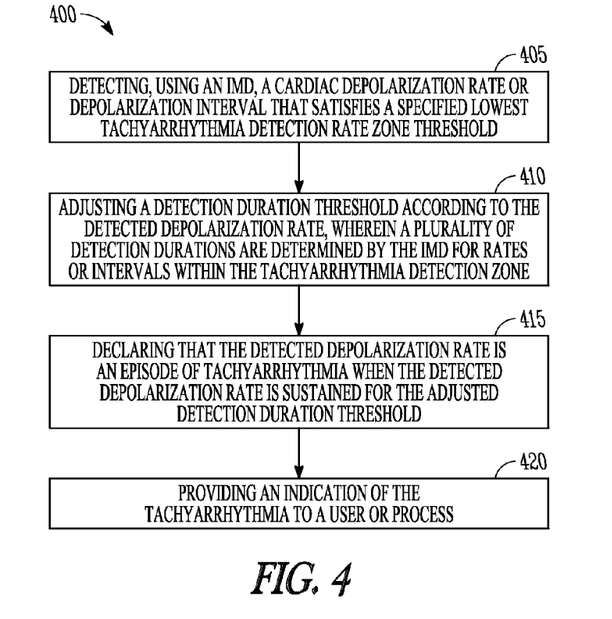
FIG. 4 is a flow diagram 400 of a method of device-based detection of tachyarrhythmia.

FIG. 4 is a flow diagram of a method 400 of device-based detection of tachyarrhythmia. At block 405, a cardiac depolarization rate or depolarization interval that satisfies a specified lowest tachyarrhythmia detection rate zone threshold is detected using the IMD. The IMD senses a cardiac depolarization signal and determines depolarization rate or interval from the signal. The IMD may determine which tachyarrhythmia detection rate zone the sensed rate or interval falls into.

At block 410, a detection duration threshold is adjusted according to the detected depolarization rate. A plurality of detection durations are determinable by the IMD for rates or intervals within the tachyarrhythmia detection zone. Each heart rate in a zone may have a unique duration, but this is not necessarily the case. In some examples, the IMD determines a detection duration threshold according to a look-up table of durations referenced by one or both of depolarization rate and depolarization interval.

In some examples, an adjusted detection duration threshold is calculated. The method 400 includes specifying a base detection duration value, and the adjusted detection duration threshold is calculated as a function of the detected depolarization rate and the base detection duration value.

For example, in FIG. 3 a base detection duration value of 60 seconds may be specified for the first tachyarrhythmia detection zone. The value may by specified by setting a programmable value or the value may be specified in firmware. The adjusted detection duration threshold is calculated by multiplying the detected rate (or difference from a base rate) by a negative constant and adding the resulting negative product to the base detection duration value. For example, if the base duration is 60 seconds at a base rate of 170 bpm and the detected rate is 200 bpm, using a constant of −1.58 yields an adjusted detection duration threshold of 60+(−1.58)(200−170)=12.6 seconds. Thus, the adjusted duration threshold is adjusted by reducing the specified base detection duration value for a tachyarrhythmia detection rate zone as a function of the detected depolarization rate.

In FIG. 3, it can be seen that the negative constant used in the calculation can be thought of as a slope for the function. In some examples, a different base detection duration value is specified for each zone. For example, in FIG. 3, a first base value (e.g., 60 seconds) is specified for the first zone, and a second base value (e.g., 12.5 seconds) is specified for the second zone. Further, different constant or slope values can be used for different zones. In FIG. 3, a first constant or slope value can be used for the first zone and a second constant or slope value can be used for the second zone. In the second zone, if the base detection duration value is 12.5 seconds, the base rate is 200 bpm, and the detected rate is 250 bpm, using a constant of −(0.2) yields an adjusted detection duration threshold of 12.5+(−0.2)(250−200)=2.5 seconds. In FIG. 3, the third zone uses a constant of zero to make the duration constant throughout the detection zone.

If the sensed depolarization is fluctuating, a continuous adjustment of the duration may cause too much variation in the detection duration threshold. This may happen for example, if the IMD under-senses the depolarization rate. Under-sensing may occur when the electrical cardiac signals are less than a sensing threshold of the sense amplifiers. Under-sensing may cause the detected depolarization intervals to fluctuate causing the duration determined for the intervals to fluctuate as well. Thus, in some examples, the initial detected depolarization rate or interval is used to set the duration. Once a rate or interval is detected that satisfies a specified lowest tachyarrhythmia detection rate threshold, that detected rate is used to determine the adjusted duration threshold and the duration threshold is not adjusted further during the possible episode.

Returning to FIG. 4, when the adjusted detection duration threshold is determined, the detected depolarization rate is declared to be an episode of tachyarrhythmia when the detected depolarization rate is sustained for a time interval exceeding the adjusted detection duration threshold at block 415. At block 420, an indication of the tachyarrhythmia is provided to a user or process when the episode is declared to be a tachyarrhythmia.

Figure 5:
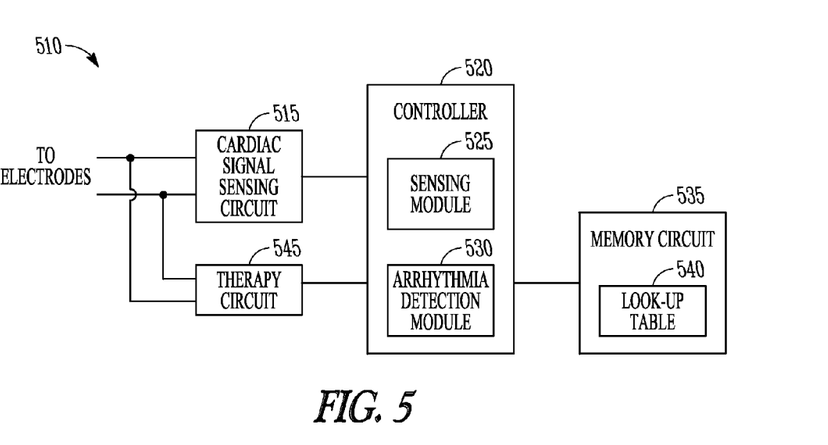
FIG. 5 is a block diagram of portions of IMD capable of detecting tachyarrhythmia.

FIG. 5 is a block diagram of portions of IMD 510 for detecting tachyarrhythmia. The IMD 510 includes an implantable cardiac signal sensing circuit 515 and a controller 520. The implantable cardiac signal sensing circuit 515 produces a sensed electrical cardiac signal representative of cardiac activity of a subject.

The controller 520 is communicatively coupled to the cardiac signal sensing circuit 515. The communicative coupling allows signals to be communicated between the controller 520 and the cardiac signal sensing circuit 515 even though there may be intervening circuitry. In some examples, the controller 520 includes a processor such as a digital signal processor, application specific integrated circuit (ASIC), microprocessor, or other type of processor, interpreting or executing instructions in software or firmware. In some examples, the controller 520 can include a state machine or sequencer that is implemented in hardware circuits. The controller 520 can include any combination of hardware, firmware, or software. The controller 520 includes modules to provide the functions described herein. These modules can include software, hardware, firmware or any combination thereof. For example, the modules can include instructions in software executing on, or interpreted by, the controller 520. Multiple functions can be performed by one or more of the modules.

The controller 520 includes a sensing module 525 to detect cardiac depolarizations using the sensed cardiac signal. In some examples, the sensing module 525 detects intervals between depolarizations by sensing R-waves. R-waves are deflections in cardiac signals that represent early depolarization of the ventricles. In certain examples, the cardiac signal sensing circuit includes a peak detector circuit to detect the R-waves.

The controller 520 also includes an arrhythmia detection module 530. The arrhythmia detection module 530 detects a depolarization rate or depolarization interval that satisfies a first tachyarrhythmia detection rate zone threshold. Tachyarrhythmia detection rate thresholds for several detection zones are typically programmable within the IMD 510. In some examples, the first tachyarrhythmia detection rate zone threshold is the lowest threshold used for detecting a possible episode of tachyarrhythmia. In certain examples, the lowest tachyarrhythmia detection threshold rate is 170 bpm. The arrhythmia detection module 530 adjusts a specified detection duration threshold for the tachyarrhythmia detection zone according to the detected depolarization rate.

In some examples, the arrhythmia detection module 530 calculates a central tendency of the depolarization rate or depolarization intervals. The central tendency may be an average of the rate or intervals, or a median value of the rate or intervals. The arrhythmia detection module 530 adjusts the detection duration threshold according to the calculated central tendency rate or interval.

The detection duration threshold is adjustable to a plurality of values for the same tachyarrhythmia detection zone. In some examples, the IMD 510 includes a memory circuit 535 integral to or communicatively coupled to the controller 520. The memory circuit 540 stores a look-up table 540 of detection duration values indexed or referenced by one or both of depolarization rate and depolarization interval. When the detected rate or interval satisfies one or more tachyarrhythmia detection thresholds, arrhythmia detection module 530 determines the adjusted detection duration threshold according to the look-up table 540.

In some examples, the adjusted detection duration threshold is calculated. The arrhythmia detection module 530 calculates the adjusted detection duration threshold as a function of the detected depolarization rate and a base detection duration value that is specified for the tachyarrhythmia detection rate zone threshold.

The IMD 510 may classify a detected tachyarrhythmia using several specified tachyarrhythmia detection rate zones. For instance, as in the example above the IMD 510 may use separate rate detection zones to detect slow VT, VT, and VF. When the arrhythmia detection module 530 determines that a detected depolarization rate falls within one of the specified tachyarrhythmia detection rate zones, the arrhythmia detection module 530 adjusts the detection duration threshold for that tachyarrhythmia rate zone according to the detected depolarization rate.

Multiple detection duration thresholds are determinable by the arrhythmia detection module within each of the tachyarrhythmia detection zones. In certain examples, the arrhythmia detection module 530 determines the detection duration thresholds using the table look-up method, and in some examples, the arrhythmia detection module 530 calculates the adjusted detection duration threshold. In some examples, the arrhythmia detection module 530 calculates the adjusted detection duration threshold using a base detection duration value, and a different base detection duration value is used for two or more of the tachyarrhythmia detection zones.

When the detected depolarization rate is present for the entire adjusted detection duration threshold, the arrhythmia detection module 530 declares that the detected depolarization rate is an episode of tachyarrhythmia. The arrhythmia detection module 530 provides an indication of the tachyarrhythmia to a user or process. In some examples, the IMD 510 includes a therapy circuit 545 communicatively coupled to the controller and configured to provide an anti-tachyarrhythmia therapy. The indication of the tachyarrhythmia may be used by the IMD 510 to begin an anti-tachyarrhythmia treatment such as anti-tachycardia pacing (ATP) or high energy electrical shock therapy. In some examples, the classification is communicated to an external device, such as an IMD programmer or advanced patient management (APM) system.

In some examples, the indication may trigger other detection methods to confirm that a patient is indeed experiencing the tachyarrhythmia corresponding to the tachyarrhythmia detection zone or to further classify the tachyarrhythmia. In certain examples, the episode is confirmed using an assessment of heart rhythm stability when a subject experiences a sudden increase in heart rate. Examples of methods and systems to detect arrhythmia and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

According to some examples, the arrhythmia detection module 530 is further able to determine a type of the tachyarrhythmia. In certain examples, the detection of tachyarrhythmia is confirmed using the morphology of the sensed depolarization signal. The morphology of a sensed cardiac depolarization is compared to a template of a known normal or abnormal depolarization morphology (such as NSR, VT, VF, or SVT) stored in the memory. Morphology-based algorithms to classify tachyarrhythmia are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference in its entirety.

In some examples, the arrhythmia detection module 530 may further adjust the detection duration threshold according to the tachyarrhythmia type. In certain examples, the arrhythmia detection module 530 compares the average ventricular contraction rate and the average atrial contraction rate. If the atrial and ventricular rates match, then there is a one-to-one association between depolarizations in the ventricle and in the atrium, and the detected arrhythmic rhythm is a one-to-one tachyarrhythmia. The arrhythmia detection module 530 may then perform a morphological analysis of the correlation between the detected tachyarrhythmia and a template waveform recorded during a known rhythm to further classify this one-to-one tachyarrhythmia as either SVT or VT with retrograde conduction. If the arrhythmia detection module 530 cannot make the determination between SVT and VT, the arrhythmia detection module 530 may extend the duration beyond the adjusted detection duration threshold.

If the average ventricular rate exceeds the average atrial rate by more than a threshold rate value (V>A), the arrhythmia detection module 530 may then perform a morphological analysis to determine whether the detected tachyarrhythmia is monomorphic VT (MVT). MVT is a tachyarrhythmia where the beats appear to match each other morphologically in contrast to a polymorphic VT where there are beat-to-beat changes in morphology. If the arrhythmia detection module 530 determines that the detected tachyarrhythmia is MVT with V>A, the arrhythmia detection module 530 may keep the adjusted detection duration threshold and not adjust the duration further. Descriptions of systems and methods for classifying detected tachycardia based on average atrial and ventricular rates calculated from selected atrial and ventricular intervals are found in Elahi et al., U.S. Pat. No. 7,346,388, entitled, "Method and Apparatus for Rate Accuracy Enhancement in Ventricular Tachycardia Detection," filed Feb. 10, 2005, which is incorporated herein by reference.

In some examples, if the average atrial rate exceeds the ventricular rate by more than a threshold rate value (A>V), the arrhythmia detection module 530 may then perform a stability analysis to determine whether to further adjust the detection duration threshold. In certain examples, the stability is assessed by measuring the degree of variability of ventricular (R-R) intervals during the tachyarrhythmia episode. The current average difference between R-R intervals may be compared to a specified stability threshold. If A>V, and the average difference in R-R intervals is greater than the specified stability threshold, the arrhythmia detection module 530 may lengthen the determined detection duration threshold. If A>V, and the average difference in R-R intervals is less than the specified stability threshold, the arrhythmia detection module 530 may shorten the determined detection duration threshold. If V>A, the arrhythmia detection module 530 does not perform a stability analysis. Examples of methods and systems to assess the stability of rhythms are found in the previously mentioned U.S. Pat. No. 6,493,579.

In some examples, the arrhythmia detection module 530 is able to determine if the tachyarrhythmia is VF (e.g., by using a morphology analysis). When the tachyarrhythmia is classified as VF, the arrhythmia detection module 530 may shorten the detection duration threshold. In certain examples, the arrhythmia detection module 530 uses further analysis to determine if the detected tachyarrhythmia is noise. When the arrhythmia detection module 530 classifies the detected arrhythmia as being signal noise rather than a tachyarrhythmia, the arrhythmia detection module 530 may lengthen the adjusted detection duration threshold.

In some examples, when the detected arrhythmia is determined to be an episode of tachyarrhythmia, the IMD 510 may use another different duration to determine whether the declared tachyarrhythmia is sustained. This duration may be referred to as sustained rate duration (SRD). The controller 520 initiates a delivery of anti-tachyarrhythmia therapy using the therapy circuit 545 in response to an expiration of the SRD and withholds the delivery of the anti-tachyarrhythmia therapy if the SRD is terminated before the expiration. Descriptions of systems and methods that implement an SRD are found in Li et al., U.S. Patent Pub. No. US-2008-005183-A1, "Method and Apparatus for Automated Adjustment of Arrhythmia Detection Duration," filed Aug. 25, 2006, which is incorporated herein by reference in its entirety.

According to some examples, when the episode of tachyarrhythmia ends, the arrhythmia detection module 530 may use yet another different time duration for re-detecting the tachyarrhythmia. This can be called a re-detection duration threshold. The arrhythmia detection module 530 declares the tachyarrhythmia episode to be re-detected when a depolarization rate or depolarization interval is detected that satisfies a tachyarrhythmia re-detection rate zone threshold.

The IMD 510 may have multiple re-detection rate zone thresholds corresponding to the tachyarrhythmia detection zones. The detected depolarization rate or interval needs to be sustained for the re-detection duration for the arrhythmia detection module 530 to declare the tachyarrhythmia to be re-detected. The arrhythmia detection module 530 may adjust the re-detection duration threshold according to the detected rate or interval. The re-detection duration threshold may differ from the initial detection duration for a given depolarization rate. In certain examples, the arrhythmia detection module 530 adjusts the re-detection duration threshold using the same look-up table as the table used in initial detection. In certain examples, a different look-up table is used for re-detection than for the initial detection. In certain examples, the arrhythmia detection module 530 adjusts the re-detection duration threshold using a different function of the depolarization rate than the function used in initial detection.

In some examples, when anti-tachyarrhythmia therapy (e.g., high energy defibrillation shock therapy) is provided, the arrhythmia detection module 530 may use still another different duration for re-detecting the tachyarrhythmia post-therapy. This can be called a post-therapy detection duration threshold. The arrhythmia detection module 530 declares the tachyarrhythmia episode to have reoccurred post-therapy when a depolarization rate or depolarization interval is detected that satisfies a tachyarrhythmia post-therapy rate zone threshold.

The IMD 510 may have multiple post-therapy re-detection rate zone thresholds corresponding to the tachyarrhythmia detection rate zones discussed previously. The arrhythmia detection module 530 adjusts a post-therapy detection duration threshold according to a detected depolarization rate.

The adjusted post-therapy duration threshold may differ from one or both of the initial detection duration and the re-detection duration for a given depolarization rate. In certain examples, the arrhythmia detection module 530 adjusts the re-detection duration threshold using the same look-up table as the table used in initial detection. In certain examples, a different look-up table is used post-therapy than a table used for one or both of the initial detection and the re-detection. In certain examples, the arrhythmia detection module 530 adjusts the post-therapy detection duration threshold using a different function of the depolarization rate than the function used in one or both of initial detection and re-detection.

Thus, the durations are more dynamic than an approach using a single duration per zone. This allows a duration to better suit the rate of the arrhythmia. For example, slower rates may have longer detection durations than faster rates, even within the same rate zone. This may help to reduce inappropriate delivery of therapy.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable cardiac signal sensing circuit configured to produce a sensed cardiac signal representative of cardiac activity of a subject;
   a controller communicatively coupled to the cardiac signal sensing circuit, wherein the controller includes:
      a sensing module configured to detect a cardiac depolarization using the sensed cardiac signal; and
      an arrhythmia detection module configured to:
         detect a detection episode in which a depolarization rate or interval satisfies a first tachyarrhythmia detection rate zone threshold;
         adjust, for the same detection episode, a specified detection duration threshold for the tachyarrhythmia detection zone according to as a function of the detected depolarization rate or interval, wherein the detection duration threshold is adjustable to a plurality of values for depolarization rates or intervals within the same tachyarrhythmia detection rate zone, and wherein the detection duration threshold is adjustable according to a different function for a different tachyarrhythmia detection zone;
         generate an indication of detection of an episode of tachyarrhythmia when the detected depolarization rate is sustained for a period of time that meets or exceeds the adjusted detection duration threshold; and
         provide the indication of the detected episode of tachyarrhythmia to a user or process; and
   a therapy circuit communicatively coupled to the controller and configured to provide an anti-tachyarrhythmia therapy,
   wherein the arrhythmia detection module is configured to determine, following expiration of the adjusted detection duration threshold, whether the declared tachyarrhythmia episode is sustained during a specified sustained rate duration (SRD), and
   wherein the controller is configured to initiate a delivery of an anti-tachyarrhythmia therapy in response to an expiration of the SRD during which the declared tachyarrhythmia episode is sustained.

2. The apparatus of claim 1, including:
   a memory circuit included with or communicatively coupled to the controller and configured to store detection duration values using depolarization rate or depolarization interval as an index; and
   wherein the arrhythmia detection module is configured to determine the detection duration threshold using a detection duration value determined using the index.

3. The apparatus of claim 1, wherein the arrhythmia detection module is configured to calculate the adjusted detection duration threshold as a function of the detected depolarization rate and a base detection duration value, wherein the base detection duration value is specified according to the tachyarrhythmia detection rate zone threshold.

4. The apparatus of claim 1, wherein the arrhythmia detection module is configured to:
   determine that a detected depolarization rate or interval falls within one of a plurality of specified tachyarrhythmia detection rate zones; and
   adjust the detection duration threshold for the tachyarrhythmia rate zone according to the detected depolarization rate or interval, wherein the arrhythmia detection module is configured to determine a plurality of detection durations within each of two or more of the tachyarrhythmia detection rate zones.

5. The apparatus of claim 4,
including a different specified base detection duration value for each of at least two of the tachyarrhythmia detection rate zones, and
wherein the arrhythmia detection module is configured to calculate an adjusted detection duration threshold as a function of the detected depolarization rate or interval and a base detection duration value for the particular tachyarrhythmia detection rate zone in which the detected depolarization rate or interval falls.

6. The apparatus of claim 5, wherein the arrhythmia detection module is configured to calculate the adjusted duration threshold by reducing the specified base detection duration value for a tachyarrhythmia detection rate zone as a function of the detected depolarization rate or interval.

7. The apparatus of claim 1, wherein the arrhythmia detection module is configured to:
calculate a central tendency of the depolarization rate or intervals; and
adjust the detection duration threshold according to the calculated central tendency.

8. The apparatus of claim 1, wherein the arrhythmia detection module is configured to:
adjust an initial detection duration threshold as a function of an initial detected depolarization rate or interval;
re-detect a tachyarrhythmia when a re-detected depolarization rate or interval satisfies a specified tachyarrhythmia re-detection rate zone threshold; and
adjust a re-detection duration threshold as a function of the re-detected depolarization rate, wherein the re-detection duration threshold is capable of being different from the initial detection duration for a given depolarization rate or interval.

9. The apparatus of claim 1, wherein the arrhythmia detection module is configured to: re-detect, after the anti-tachyarrhythmia therapy ceases, a depolarization rate or interval that satisfies a specified tachyarrhythmia re-detection rate zone threshold; and adjust a post-therapy detection duration threshold as a function of the re-detected depolarization rate or interval, wherein the arrhythmia detection module is configured to be capable of calculating the post-therapy detection duration threshold as a different function of the depolarization rate or interval than an initial detection duration threshold.

10. The apparatus of claim 1, wherein the arrhythmia detection module is configured to:
classify the tachyarrhythmia; and
adjust the detection duration threshold according to the determined tachyarrhythmia classification.

11. A method comprising:
detecting, using an IMD, a detection episode in which a cardiac depolarization rate or interval that satisfies a specified tachyarrhythmia detection rate zone threshold;
adjusting, for the same detection episode, a detection duration threshold according to as a function of the detected depolarization rate or interval, wherein the detection duration threshold is adjustable to a plurality of values for depolarization rates or intervals within the tachyarrhythmia detection zone, and wherein the detection duration threshold is adjustable according to a different function for a different tachyarrhythmia detection zone;
generating an indication that the detected depolarization rate is an episode of tachyarrhythmia when the detected depolarization rate is sustained for a period of time that meets or exceeds the adjusted detection duration threshold;
determining, following expiration of the adjusted detection duration threshold, whether the declared tachyarrhythmia episode sustains during a specified sustained rate duration (SRD);
initiating a delivery of an anti-tachyarrhythmia therapy in response to an expiration of the SRD during which the declared tachyarrhythmia episode is sustained; and
providing the indication of the detected episode of tachyarrhythmia to a user or process.

12. The method of claim 11, wherein adjusting the detection duration threshold includes determining the adjusted detection duration threshold according to an index by the detected depolarization rate or interval.

13. The method of claim 11, including:
specifying a base detection duration value, and
wherein adjusting the detection duration threshold includes calculating the adjusted detection duration threshold as a function of the detected depolarization rate or interval and the base detection duration value.

14. The method of claim 11, including:
determining that the detected depolarization rate falls within one of a plurality of specified tachyarrhythmia detection rate zones; and
declaring detection of an episode of tachyarrhythmia when the detected depolarization rate is sustained for a time interval that meets or exceeds the adjusted detection duration threshold for the tachyarrhythmia detection rate zone into which detected depolarization rate falls, wherein determining the detection duration comprises using one of a plurality of detection durations that are determinable for depolarization rates or intervals within a single tachyarrhythmia detection rate zone.

15. The method of claim 14,
including specifying a different base detection duration value for different tachyarrhythmia detection rate zones, and
wherein adjusting the detection duration threshold includes calculating the adjusted detection duration threshold as a function of the detected depolarization rate or interval and the base detection duration value for the tachyarrhythmia rate zone into which detected depolarization rate falls.

16. The method of claim 15, wherein adjusting the detection duration threshold includes reducing the specified base detection duration value as a function of the detected depolarization rate or interval.

17. The method of claim 11, wherein adjusting a detection duration threshold according to the detected depolarization rate or interval includes:
calculating a central tendency of the depolarization rate or intervals; and
adjusting the detection duration threshold according to the calculated central tendency.

18. The method of claim 11,
wherein adjusting a detection duration threshold includes adjusting an initial detection duration threshold as a function of an initial detected depolarization rate or interval, and
wherein the method includes:
re-detecting a tachyarrhythmia when a re-detected depolarization rate or satisfies a specified tachyarrhythmia re-detection rate zone threshold; and
adjusting a re-detection duration threshold as a function of the re-detected depolarization rate, wherein the re-detection duration threshold is capable of being different from the initial detection duration threshold for a given depolarization rate or interval.

19. The method of claim 11, including: re-detecting, after the anti-tachyarrhythmia therapy ceases, a depolarization rate or interval that satisfies a specified tachyarrhythmia re-detection rate zone threshold; and adjusting a post-therapy duration detection threshold as a function of the re-detected depolarization rate or interval, wherein the post-therapy detection duration threshold is capable of being calculated as a different function of the depolarization rate or interval than the initial detection duration threshold.

20. The method of claim 11, including classifying the tachyarrhythmia, and wherein adjusting a detection duration threshold includes adjusting the detection duration threshold according to the determined tachyarrhythmia classification.

21. An apparatus comprising:
an implantable cardiac signal sensing circuit configured to produce a sensed cardiac signal representative of cardiac activity of a subject; and
a controller communicatively coupled to the cardiac signal sensing circuit, wherein the controller includes:
 a sensing module configured to detect a cardiac depolarization using the sensed cardiac signal; and
 an arrhythmia detection module configured to:
  detect a detection episode in which a depolarization rate or interval that satisfies a first tachyarrhythmia detection rate zone threshold;
  adjust, for the same detection episode, a specified detection duration threshold for the tachyarrhythmia detection zone as a function of the detected depolarization rate or interval, wherein the detection duration threshold is adjustable to a plurality of values for depolarization rates or intervals within the same tachyarrhythmia detection rate zone, and wherein the detection duration threshold is adjustable according to a different function for a different tachyarrhythmia detection zones;
  generate an indication of detection of an episode of tachyarrhythmia when the detected depolarization rate is sustained for a period of time that meets or exceeds the adjusted detection duration threshold; and
  provide the indication of the detected episode of tachyarrhythmia to a user or process;
 a memory circuit included with or communicatively coupled to the controller and configured to store detection duration values using depolarization rate or depolarization interval as an index, wherein the arrhythmia detection module is configured to determine the detection duration threshold using a detection duration value determined using the index; and
 a therapy circuit communicatively coupled to the controller and configured to provide an anti-tachyarrhythmia therapy, wherein the arrhythmia detection module is configured to determine, following expiration of the adjusted detection duration threshold, whether the declared tachyarrhythmia episode is sustained during a specified sustained rate duration (SRD), and wherein the controller is configured to initiate a delivery of an anti-tachyarrhythmia therapy in response to an expiration of the SRD during which the declared tachyarrhythmia episode is sustained.

22. The apparatus of claim 21, wherein the arrhythmia detection module is configured to:
re-detect, after the anti-tachyarrhythmia therapy ceases, a depolarization rate or interval that satisfies a specified tachyarrhythmia re-detection rate zone threshold; and
adjust a post-therapy detection duration threshold as a function of the re-detected depolarization rate or interval, wherein the arrhythmia detection module is configured to be capable of calculating the post-therapy detection duration threshold as a different function of the depolarization rate or interval than an initial detection duration threshold.

* * * * *